US012727862B2

(12) United States Patent
Selbekk

(10) Patent No.: US 12,727,862 B2
(45) Date of Patent: Sep. 8, 2026

(54) ULTRASOUND IMAGE ARTEFACT REDUCTION

(71) Applicant: Sonoclear AS, Oslo (NO)

(72) Inventor: Tormod Selbekk, Oslo (NO)

(73) Assignee: Sonoclear AS, Oslo (NO)

( * ) Notice: Subject to any disclaimer, the term of this patent is extended or adjusted under 35 U.S.C. 154(b) by 0 days.

(21) Appl. No.: 18/862,405

(22) PCT Filed: May 12, 2023

(86) PCT No.: PCT/EP2023/062836
§ 371 (c)(1),
(2) Date: Nov. 1, 2024

(87) PCT Pub. No.: WO2023/218067
PCT Pub. Date: Nov. 16, 2023

(65) Prior Publication Data
US 2025/0288282 A1 Sep. 18, 2025

(30) Foreign Application Priority Data
May 12, 2022 (GB) ..................................... 2206969

(51) Int. Cl.
*A61B 8/00* (2006.01)
*G06T 5/70* (2024.01)
(Continued)

(52) U.S. Cl.
CPC ............ *A61B 8/5269* (2013.01); *A61B 8/469* (2013.01); *G06T 5/70* (2024.01); *G06V 10/25* (2022.01);
(Continued)

(58) Field of Classification Search
CPC ..... A61B 8/5269; A61B 8/469; A61B 8/5223; A61B 8/085; G06T 5/70;
(Continued)

(56) References Cited

U.S. PATENT DOCUMENTS 4,542,745 A 9/1985 Oakley et al.
5,625,137 A 4/1997 Madsen et al.
(Continued)

FOREIGN PATENT DOCUMENTS

EP 0298293 B1 3/1994
EP 1671656 A1 6/2006
(Continued)

OTHER PUBLICATIONS

KR-101120816 machine translation (Year: 2012).*
(Continued)

*Primary Examiner* — Alexei Bykhovski

(57) ABSTRACT

There is provided a method and system (1) for reducing an artefact (10) in an ultrasound image (4) of biological tissue (5), the biological tissue (5) comprising an object (6) that has different attenuation than surrounding tissue (8), wherein the object (6) comprises a cyst, a ventricle, a fluid-filled cavity, or a natural or surgically-created opening. The method comprises: obtaining an ultrasound image (4) of the biological tissue (5) including the object (6) that has different attenuation than the surrounding tissue (8); identifying the object (6) in the ultrasound image (4); identifying a region (14) of the ultrasound image (4) that has an enhancement or shadowing artefact (10) caused by the different attenuation of the object (6), wherein the region (14) is identified based on one or more of: geometry of a transducer (2) used to obtain the ultrasound image (4), a beam angle of transmitted ultrasound pulse(s) (22) used to obtain the ultrasound image (4), and a distance of propagation of the ultrasound pulse(s) (22) in the object (6); and applying a spatially varying gain correction to the identified region (14) to compensate for the difference in attenuation of the object (6).

14 Claims, 4 Drawing Sheets

(51) Int. Cl.

| | |
|---|---|
| ***G06V 10/25*** | (2022.01) |
| ***G06V 10/26*** | (2022.01) |
| ***G16H 10/40*** | (2018.01) |

(52) U.S. Cl.

CPC ............. *G06V 10/26* (2022.01); *G16H 10/40* (2018.01); *G06T 2207/10132* (2013.01); *G06T 2207/30004* (2013.01); *G06V 2201/03* (2022.01)

(58) Field of Classification Search

CPC ........... G06T 2207/10132; G06T 2207/30004; G06V 10/25; G06V 10/26; G06V 2201/03; G16H 10/40

See application file for complete search history.

(56) References Cited

U.S. PATENT DOCUMENTS

| | | | | |
|---|---|---|---|---|
| 5,644,429 | A | 7/1997 | Alfano et al. | |
| 6,302,848 | B1 | 10/2001 | Larson et al. | |
| 6,475,800 | B1 | 11/2002 | Hazen et al. | |
| 9,770,521 | B2 | 9/2017 | Selbekk et al. | |
| 10,531,803 | B2 | 1/2020 | Pan et al. | |
| 2004/0142905 | A1 | 7/2004 | Wang | |
| 2005/0074407 | A1 | 4/2005 | Smith | |
| 2015/0118161 | A1* | 4/2015 | Selbekk | A61K 49/22 424/9.1 |
| 2016/0278743 | A1* | 9/2016 | Kawashima | G16H 10/40 |
| 2018/0068590 | A1* | 3/2018 | Mattausch | G06T 15/06 |
| 2020/0330076 | A1* | 10/2020 | Weber | G01S 7/52033 |
| 2021/0224996 | A1* | 7/2021 | Tsutaoka | G06V 10/764 |
| 2022/0087653 | A1* | 3/2022 | Huang | G01S 7/52036 |
| 2024/0029245 | A1* | 1/2024 | Xu | A61B 8/0858 |
| 2024/0415490 | A1 | 12/2024 | Glomm et al. | |

FOREIGN PATENT DOCUMENTS

| | | | | |
|---|---|---|---|---|
| EP | 1842559 | A1 | 10/2007 | |
| EP | 3466342 | A1 | 4/2019 | |
| GB | 1005750 | A | 9/1965 | |
| KR | 101120816 | B1 * | 3/2012 | A61B 8/469 |
| WO | WO-9220241 | A1 | 11/1992 | |
| WO | WO-9421301 | A1 | 9/1994 | |
| WO | WO-9505854 | A1 | 3/1995 | |
| WO | WO-0158344 | A1 | 8/2001 | |
| WO | WO-2008120249 | A1 | 10/2008 | |
| WO | WO-2008137944 | A1 | 11/2008 | |
| WO | WO-2009013692 | A2 | 1/2009 | |
| WO | WO-2009056857 | A1 | 5/2009 | |
| WO | WO-2013167654 | A1 | 11/2013 | |
| WO | WO-2014012042 | A1 | 1/2014 | |
| WO | WO-2014116646 | A1 | 7/2014 | |
| WO | WO-2022258727 | A1 | 12/2022 | |
| WO | WO-2023094491 | A1 | 6/2023 | |
| WO | WO-2023218067 | A1 | 11/2023 | |
| WO | WO-2024241296 | A1 | 11/2024 | |

OTHER PUBLICATIONS

Akaishi, T., et al., "Osmotic pressure of serum and cerebrospinal fluid in patients with suspected neurological conditions", Neural Regeneration Research (2020); 15(5): 944-947.

[Author Unknown] "Breast Tumors, Malignant", Focused Ultrasound Foundation (Aug. 5, 2024) [online] https://www.fusfoundation.org/diseases-and-conditions/breast-tumors-malignant/#:~:text=Focused%20ultrasound%20 (Access Date: Sep. 4, 2024); 11 pages.

[Author Unknown] "Lecithin", Drugs.com (Aug. 11, 2023); 3 pages.

[Author Unknown] "Otsulip 10%, 20% Soybean Oil (C14-24) Fat Emulsion injection", Otsuka, Manufactured by Guangdong Otsuka Pharmaceutical Co., Ltd., Foshan, Guangdong [online] https://otsuka.co.id/storage/app/media/product_photos/cn-iv-solution/Update%20PI%20BFLUID%20PTOI_website.pdf (Access Date: Oct. 10, 2024); 4 pages.

Azhari, H., "Appendix A Typical Acoustic Properties of Tissues", Basics of biomedical ultrasound for engineers, John Wiley & Sons (2010); 313-314.

Bacon, D. R., "Primary calibration of ultrasonic hydrophone using optical interferometry", IEEE Trans Ultrason Ferroelectr Freq Control (1988); 35(2):152-161. doi: 10.1109/58.4165.

Burrin, D. G., et al., "Impact of New-Generation Lipid Emulsions on Cellular Mechanisms of Parenteral Nutrition-Associated Liver Disease1-3", American Society for Nutrition Advanced (2014); 5: 82-91. doi:10.3945/an.113.004796.

Butte, P. V., et al., "Near-infrared imaging of brain tumors using the Tumor Paint BLZ-100 to achieve near-complete resection of brain tumors", Neurosurgical Focus (2014); 36(2): E1; 8 pages.

Database PubChem, Compound Summary: 2-[2-[3,4-Bis(2-hydroxyethoxy)oxolan-2-yl]-2-(2-hydroxyethoxy)ethoxy]ethyl octadec-9-enoate, CID 443315; created Jun. 24, 2005, modified Sep. 28, 2024; U.S. National Library of Medicine, National Center for Biotechnology Information [online] https://pubchem.ncbi.nlm.nih.gov/compound/443315 (Access Date: Oct. 2, 2024); 46 pages.

Database PubChem, Compound Summary: Glycerin, CID 753; created Nov. 29, 2005, modified Sep. 28, 2024; U.S. National Library of Medicine, National Center for Biotechnology Information [online] https://pubchem.ncbi.nlm.nih.gov/compound/753 (Access Date: Oct. 2, 2024); 162 pages.

Database PubChem, Compound Summary: Lecithin, CID 5287971; created Sep. 16, 2004, modified Sep. 28, 2024;U.S. National Library of Medicine, National Center for Biotechnology Information [online] https://pubchem.ncbi.nlm.nih.gov/compound/5287971 (Access Date: Oct. 2, 2024); 71 pages.

Database PubChem, Compound Summary: Soybean Oil, SID 481190644, U.S. National Library of Medicine, National Center for Biotechnology Information [online] https://pubchem.ncbi.nlm.nih.gov/compound/Soybean-Oil (Access Date: Oct. 2, 2024); 53 pages.

Duck, F. A., "Propagation of sound through tissue", The Safe Use of Ultrasound in Medical Diagnosis, London (2000); pp. 4-15; 8 pages.

Dupont, C., et al., "A novel device for intraoperative photodynamic therapy dedicated to glioblastoma treatment", Future Oncology (2017); 13(27): 2441-2454.

Dupont, C., et al., "INtraoperative photoDYnamic Therapy for GliOblastomas (INDYGO): study protocol for a phase I clinical trial", Neurosurgery (2019); 84(6): E414-E419.

Eldor, J., "Combined Spinal Epidural Catheters for Epidural Cooling, Cerebrospinal Fluid Aspiration and Spinal Intralipid Infusion for Treatment of Spinal and Brain Injuries, Diseases and Protection", Open Journal of Anesthesiology (2014); 2014(4): 13-30.

Griffin, W. C., "Calculation of HLB values of non-ionic surfactants", Journal of Society of Cosmetic Chemists, Meeting, New York City (May 14, 1954): 249-256.

Griffin, W. C., "Classification of surface-active agents by"HLB"", Journal of Society of Cosmetic Chemists, Meeting, Chicago Chapter, Chicago, IL (Oct. 11, 1949); 1: 311-326.

Hildell, J. G., et al., "New intravesical contrast medium for CT: preliminary studies with arachis (peanut) oil", American Journal of Roentgenology (1981); 137(4): 777-780.

Hu, Y., et al., "A light blanket for intraoperative photodynamic therapy", Photodynamic Therapy: Back to the Future, Proc. of SPIE (2009); 7380: 73801W-1-73801W-9.

International Preliminary Report on Patentability for International Application No. PCT/EP2022/083056, by Sonoclear AS, mailed Jun. 6, 2024, 7 pages.

International Search Report and Written Opinion for PCT Application No. PCT/EP2022/083056, by Sonoclear AS, mailed Mar. 7, 2023, 8 pages.

International Search Report and Written Opinion for PCT Application No. PCT/EP2023/062836, by Sonoclear AS, mailed Aug. 17, 2023, 10 pages.

International Search Report and Written Opinion for PCT Application No. PCT/IB2024/055100, by Sonoclear AS, mailed Sep. 18, 2024, 16 pages.

(56) References Cited

OTHER PUBLICATIONS

International Search Report and Written Opinion for PCT Application No. PCT/IB2024/057054, by Sonoclear AS, mailed Nov. 11, 2024, 18 pages.
Intralipid® 20% A 20% I.V. Fat Emulsion Tablets: 150 mg, 100 mg, Label; Highlights of Prescribing Information, Medication Guide approved by the US. Food and Drug Administration; Revised: Jan. 2018 (Jan. 2018), Initial U.S. Approval: 2014, Reference ID: 4021443, Distributed by: AstraZeneca Pharmaceuticals LP, Wilmington, DE, USA, 30 pages.
Kaye & Laby, "Tables of Physical & Chemical Constants", National Physics Laboratory, UK (May 7, 2019) [online] https://web.archive.org/web/20190507172955/http://www.kayelaby.npl.co.uk/toc/ [Access Date: Dec. 6, 2024]; 5 pages.
Laroche, M., et al., "Invasive Neuromonitoring Techniques", Cerebral Trauma and Stroke, Atlas of Emergency Neurosurgery (2015); pp. 101-118.
Liu, Y., et al., "Nontoxic Intralipid-DSPE-PEG2000-COOH Nanoparticles as Optical Coherence Tomography Contrast Agents for Tumor Angiography in Live Animals", ACS Applied Nano Materials (2023); 6(19): 17691-17697.
Mahmoudi, K., et al., "5-aminolevulinic acid photodynamic therapy for the treatment of high-grade gliomas", Journal of Neuro-oncology (2019); 141: 595-607.
Mashoufi, R., et al., "Interventional radiology for disease management: a narrative review", Cureus (2023); 15(11): e48603; 8 pages.
Meerbaum, S., "Myocardial Contrast Two-dimensional Echocardiography", Kluwer Academic Publishers (1989); p. 72; 10 pages.
Search Report under Section 17(5) for Great Britain Patent Application No. 2116863.8, by Sonoclear AS, mailed Aug. 1, 2022, 3 pages.
Shih, J. J., et al., "Brain-computer interfaces in medicine", Mayo Clinic Proceedings (Mar. 2012); 87(3): 268-279.
Sterile Water for Injection, USP, in VIAFLEX Plastic Container, for Drug Diluent Use Only, Labeling-Package Insert approved by the U.S. Food and Drug Administration; Revised: Sep. 2014 (Sep. 2014), Reference ID: 3937352, Distributed in Canada by Baxter Corporation, Mississauga, ON L5N 0C2; 8 pages.
Theek, B., et al., "Emerging methods in radiology", Der Radiologe (2020); 60(Suppl 1): S41-S53.
Treece, G., et al., "Ultrasound attenuation measurement in the presence of scatterer variation for reduction of shadowing and enhancement", IEEE Transactions on Ultrasonics, Ferroelectrics, and Frequency Control, IEEE, USA (2005); 52(12): 2346-2360.
Treece, G., et al., "Ultrasound compounding with automatic attenuation compensation using paired angle scans", Ultrasound in Medicine & Biology (2007); 33(4): 630-642.
Vermandel, M., et al., "Standardized intraoperative 5-ALA photodynamic therapy for newly diagnosed glioblastoma patients: a preliminary analysis of the INDYGO clinical trial", Journal of Neuro-oncology (2021); 152: 501-514.
Wang, J., et al. "Assessment of optical clearing induced improvement of laser speckle contrast imaging", Journal of Innovative Optical Health Sciences (2010); 3(03): 159-167.
Weichenthal, M., et al., "The velocity of ultrasound in human primary melanoma tissue-implications for the clinical use of high resolution sonography", BMC Dermatology (2001); 1(1): 1-5.
Zeqiri, B., "Reference liquid for ultrasonic attenuation", Ultrasonics (1989); 27(5): 314-315.
Zhang, H., et al., "Exogenous near-infrared fluorophores and their applications in cancer diagnosis: biological and clinical perspectives", Expert Opinion on Medical Diagnostics (2011); 5(3): 241-251.
Zhang, S., et al., "Photoacoustic imaging of living mice enhanced with a low-cost contrast agent", Biomedical Optics Express (2019); 10(11): 5744-5754.
U.S. Appl. No. 18/712,472, filed May 22, 2024, by Wilhelm et al.

* cited by examiner

ULTRASOUND IMAGE ARTEFACT REDUCTION

CROSS REFERENCE TO RELATED APPLICATIONS

This application is a U.S. National Stage application under U.S.C § 371 of International Application No. PCT/EP2023/062836, filed May 12, 2023, which claims the benefit of and priority to GB Patent Application No. 2206969.4, filed May 12, 2022, the entire contents of each of which is incorporated herein by reference in its entirety.

The present invention relates to a method and a system for reducing artefacts in an ultrasound image, particularly in relation to ultrasound images of biological tissue.

Medical ultrasound imaging is frequently used for diagnostics and interventional guidance. Ultrasound imaging is a pulse-echo technique in which an ultrasound pulse is transmitted from a transducer towards biological material (e.g. tissue) and the echo originating from the biological material is received by the transducer. The ultrasound system converts the received signals into an image which is then displayed. The ultrasound image is usually presented as a grey-scale image, where the strongest echoes received by the scanner have the highest pixel intensities (i.e. brightest appearance) in the image.

The echoes may be generated from scattered sound or sound being reflected from interfaces between different organs or tissues. The amplitude of the reflected echo is dependent on the acoustic properties of the tissues and the strength of the incoming sound pulse at the interface. The strength of the incoming sound pulse is dependent on the strength of the pulse as emitted from the transducer and the attenuation of the pulse in the medium or tissue the pulse is propagating in before being reflected or scattered. The attenuation can be caused by scattering of sound from particles and/or by absorption where part of the acoustic energy is transformed to heat.

If the imaged medium contains one or more objects that have a different attenuation than the surrounding tissue, this will affect the strength of the echoes originating below the object. "Below" is typically defined in reference to an ultrasound image oriented such that the transducer surface is at the top of the image pointing downwards.

If the attenuation in the object is low compared to the surrounding tissue, the echoes below the object will be stronger than echoes at the same image depths (i.e. the same distance from the transducer in the axial direction) in the surrounding tissue. This effect may be referred to as an "enhancement artefact", showing higher pixel intensities below the given object in the ultrasound image. This is typically seen below fluid filled cavities in an organ, such as cysts or necrotic tissue. It can also be seen below saline/water-filled surgical cavities in intraoperative ultrasound imaging. Another example is in endocavity ultrasound imaging, where imaging is performed using a transducer within a water filled balloon or a transducer drape filled with gel and the distance from the transducer to the tissue is varying.

If the attenuation in the object is high compared to the surrounding tissue, the echoes below the object will be weaker and hence the pixel intensities below the object will be lower than echoes at the same image depths in the surrounding tissue. This is often referred to as a "shadowing artefact".

Such imaging artefacts can make the ultrasound images more difficult to interpret because identical tissue might be represented with different pixel intensities in the ultrasound image. This can make it difficult for medical professionals to distinguish tissue types and thus make it challenging to use the ultrasound image to make accurate diagnoses of medical conditions.

There is therefore a need to provide a way of reducing the appearance of such imaging artefacts in ultrasound images.

In a first aspect of the present invention, there is provided a method for reducing an artefact in an ultrasound image of biological tissue, the biological tissue comprising an object that has different attenuation than surrounding tissue. This may be, for example, wherein the object comprises a cyst, a ventricle, a fluid-filled cavity, or a natural or surgically-created opening; the method comprising: obtaining an ultrasound image of the biological tissue including the object that has different attenuation than the surrounding tissue; identifying the object in the ultrasound image; identifying a region of the ultrasound image that has an enhancement or shadowing artefact caused by the different attenuation of the object, wherein the region is identified by any appropriate method, such as based on one or more of: geometry of a transducer used to obtain the ultrasound image, a beam angle of transmitted ultrasound pulse(s) used to obtain the ultrasound image, and a distance of propagation of the ultrasound pulse(s) in the object; and applying a spatially varying gain correction to the identified region to compensate for the difference in attenuation of the object.

The present method thus compensates for the effect of different (i.e. heterogeneous) acoustic properties in the biological tissue by identifying the specific region of the image affected by the differing acoustic properties of the object and applying a gain correction to said region. Once the shadowing or enhancement artefact has been reduced, the tissue structures of the biological tissue may be more clearly represented in the ultrasound image thus enabling the corrected image to be used to make medical diagnoses with improved accuracy. For example, in some cases, one or more anatomical structures may have been masked or hidden by the image artefact in the original ultrasound image, and the gain correction applied to the identified region may reveal these structures by reducing the artefact.

The method may include the step of obtaining the ultrasound image using an ultrasound transducer. Thus, obtaining the ultrasound image may comprise placing an ultrasound transducer of an ultrasound scanner (also referred to as an ultrasound imaging system) in a suitable location for obtaining images of the biological tissue, and using the ultrasound transducer to obtain the ultrasound image by transmitting one or more ultrasound pulses. The ultrasound scanner may then transmit the ultrasound image data to a computer or other suitable system for image processing, e.g. for carrying out the subsequent steps of the method (such as identifying the object, identifying the region, and/or applying the gain correction). The ultrasound scanner may be a part of the image processing (e.g. computer) system (i.e. the computer system may comprise the ultrasound scanner) or they may be separate systems.

The method may be used when performing ultrasound imaging through surgical cavities or in natural body openings, e.g. open surgical, endoscopic, gynaecologic, rectal, transoesophageal ultrasound, etc.

The gain correction may be applied in real-time to the ultrasound scanner used to obtain the ultrasound image. The method may comprise subsequently (after the gain correction has been applied) using the ultrasound scanner to obtain a second ultrasound image of the biological tissue including the object. In this case, the ultrasound image may therefore be termed a first ultrasound image. Since the gain correction has been applied to the ultrasound scanner, artefacts caused by the differing attenuation of the object may therefore have a reduced appearance in the second ultrasound image compared to the first ultrasound image.

Alternatively, the method may be applied to an ultrasound image that has already been captured or recorded. In this case, obtaining the ultrasound image may comprise receiving image data representative of the ultrasound image. For instance, a computer system may receive the ultrasound image data, e.g. directly from an ultrasound scanner or from a stored data file. The computer system may then carry out the subsequent steps of the method (e.g. the identifying the object, identifying the region, and/or applying the gain correction) by processing the recorded ultrasound image using computer-implemented image processing techniques. The computer system may comprise a processor configured for this purpose, i.e. to receive and process the image data. Thus, the method may be carried out using a computer system which is configured to obtain the image data and perform the subsequent image processing steps.

Identifying the object in the ultrasound image may comprise detecting a boundary of the object, e.g. using one or more image segmentation methods. The image segmentation method(s) may be based on machine learning, model based methods, threshold segmentation, region growing methods, edge enhancement and edge detection methods, and/or any other suitable methods for detecting the object. The boundary detection may be based on a combination of these methods. The biological tissue may comprise more than one object that has different attenuation than surrounding tissue, and thus the method may comprise identifying the boundary of each object in the ultrasound image.

The region of the ultrasound image that has an enhancement or shadowing artefact caused by the different attenuation of the object may be referred to as a region of interest. If there are multiple objects in the image that have different attenuation than surrounding tissue then there may be multiple regions of interest, e.g. each object may have a corresponding region of interest. The image artefact reduction method described herein may be applied to each of the regions of interest.

In some examples, the region may be identified based on mirroring the propagation of the ultrasound pulse(s) within the object with respect to the detected boundary of the object. For instance, the method may comprise, for each ultrasound pulse of a plurality of ultrasound pulses used to obtain the ultrasound image: determining the direction of travel of the ultrasound pulse (i.e. the beam angle), determining the distance of propagation of the ultrasound pulse in the object, and reflecting (i.e. mirroring) the beam trajectory (i.e. the path of the ultrasound pulse within the object) around the boundary of the object. The beam trajectory is preferably mirrored around a lower boundary of the object, since the shadowing or enhancement artefact to be captured within the identified region is typically located below the object. As noted previously (and as used throughout this disclosure unless otherwise indicated or necessary), the terms “lower” and “below” refer to directions in an ultrasound image oriented such that the transducer is at the top of the image pointing downwards.

The invention is applicable for various transducer geometries and technologies and is not limited in this respect. Examples of transducer geometries include a flat linear array (propagation of sound in the axial direction of the transducer) and a curved linear array (propagation with a given angle defined by a curved transducer array). The geometry of the transducer may for instance be used to determine the beam angle of the ultrasound pulses.

By identifying the region to which the gain correction is applied using one or more of the geometry of the transducer used to obtain the ultrasound image, a beam angle of transmitted ultrasound pulse(s) used to obtain the ultrasound image, and a distance of propagation of the ultrasound pulse(s) in the object, the method can be applied in different situations and tailored to the specific arrangement. For instance, the method can be applied to ultrasound images taken with different transducer geometries and/or orientations, and to images of biological tissue having objects with different geometries. Additionally, the gain correction is applied to a targeted area of the image that is most likely to contain the enhancement or shadowing artefact because the artefact is typically dependent on the spatial relationship between the object and transducer, and the region identification is tailored to the specific object and/or transducer geometry.

The gain correction applied to the identified region may be referred to as a gain correction factor. The method may comprise determining or calculating the gain correction to be applied to the identified region. The correction factor may be analytically derived (i.e. calculated) or estimated from the ultrasound image. The calculations can have values of attenuation coefficients that are assumed or based on empirical data for a given soft tissue material.

An ideal gain correction may be one which, when applied to the identified region, exactly compensates for the different attenuation of the object, thus removing the shadowing or enhancement artefact completely. However, achieving an ideal gain correction may be challenging in practice. Therefore, the gain correction may at least partially compensate for the different attenuation of the object, thus reducing the appearance of the shadowing or enhancement artefact.

As well as being spatially-varying, the gain correction may be frequency dependent, e.g. dependent upon the frequency of the transmitted ultrasound pulse(s) used to obtain the ultrasound image.

The gain correction factor may be determined based on various factors. Some examples are described below. The gain correction may be determined based on any of these examples and/or a combination thereof, or in any other suitable manner.

In some examples, the gain correction may be determined based on a time of travel of the ultrasound pulse(s) at a given depth and a time of travel of the ultrasound pulse(s) in the object.

In some examples, the gain correction may be determined based on pixel intensities in one or more surrounding areas of the ultrasound image that are not affected by the enhancement or shadowing artefact. For instance, the gain correction may be based on minimising a difference in intensity (e.g. pixel intensity) between a first area of the ultrasound image that is not affected by the artefact and a second area of the ultrasound image that is affected by the artefact. By calculating a gain correction that minimises the difference in intensities between these areas, the identified region is modified to approximate the brightness of the unaffected areas, thus compensating for the effect of the object attenuation.

The first and second areas are preferably at a similar depth, i.e. a similar distance from the transducer surface. This is because in an ultrasound image of a homogeneous material these areas would typically have similar intensities (brightness) since the ultrasound pulses would have travelled the same distance in the same medium and thus been attenuated by the same amount. Therefore, selecting a gain correction that adjusts the intensity of the first area to approximate the intensity of the second area at a similar depth provides a more accurate compensation for the object attenuation.

The first area may comprise multiple areas positioned in a grid arrangement. The second area may also comprise multiple areas positioned in a grid arrangement, preferably corresponding to the grid arrangement of the first area. This may improve the accuracy of the gain correction by increasing the number of compared sites. In other examples, the first area may comprise one or more windows sliding over the identified region. Thus, the first area may cover a larger overall area whilst only requiring comparison of a small area for each step.

In another example, the gain correction factor for a pixel at depth (z) and lateral position (x) in the ultrasound image may be determined based on the sum of attenuation experienced by the ultrasound pulses contributing to the given pixel intensity. The sum of attenuation may be calculated based on known or assumed attenuation coefficients of the biological tissue along a given path of the ultrasound pulse (s) that contribute to the given pixel intensity. That is, as the ultrasound pulse travels from the transducer to the point in the biological tissue represented by the given pixel, it may travel through various types of tissue and may undergo varying amounts of attenuation in each tissue. The attenuation of each tissue type may be known or assumed. Thus, the method may comprise summing the amount of attenuation of the ultrasound pulse through each portion of the path of the ultrasound pulse, based on the known or assumed attenuations of each tissue type through which the pulse travels.

By this approach (i.e. estimating the total attenuation based on known or relative differences in attenuation coefficients of the media) it is possible to adjust the intensity to compensate for the attenuation in the object for any given received echo or pixel intensity in the ultrasound image. The gain correction may be defined as the inverse of the found attenuation.

In some examples the gain correction may be based on the apparent difference in attenuation for an ultrasound pulse propagating in the biological tissue including the object and the surrounding tissue compared to an ultrasound pulse propagating an equivalent distance in a homogeneous tissue, the homogenous tissue having the same attenuation coefficient as the surrounding tissue. In this way, the actual pulse attenuation is compared to an equivalent pulse that is not affected by the different attenuation of the object. The apparent difference in attenuation may be calculated as:

$$\mathrm{ATN\_D}(R) = (A1 - A0) * (L1 - R) * f0 \quad (1)$$

wherein R is the distance along the ultrasound pulse trajectory away from the point at which the ultrasound pulse exits the object, A1 is the attenuation coefficient of the object, A0 is the attenuation coefficient of the surrounding tissue and the homogeneous tissue, L1 is the distance the ultrasound pulse travels in the object along the given trajectory, and f0 is the frequency of the ultrasound pulse.

The gain correction can be applied to all echoes received along a given beam angle within the identified region. The gain correction is preferably applied to echoes received along multiple beam angles and/or to multiple ultrasound pulses within the identified region to increase the area that the correction is applied to.

As described previously, the method may be partially or completely carried out using a computer system and/or software.

Viewed from a second aspect, the present invention provides a computer programme product comprising instructions that, when executed, will configure a computer system to carry out the method of the first aspect.

Thus, the computer programme product of this aspect may configure the computer system to: obtain an ultrasound image of the biological tissue including the object that has different attenuation than the surrounding tissue; identify the object in the ultrasound image; identify a region of the ultrasound image that has an enhancement or shadowing artefact caused by the different attenuation of the object, wherein the region is identified based on one or more of: geometry of a transducer used to obtain the ultrasound image, a beam angle of transmitted ultrasound pulse(s) used to obtain the ultrasound image, and a distance of propagation of the ultrasound pulse(s) in the object; and apply a spatially varying gain correction to the identified region to compensate for the difference in attenuation of the object.

The instructions may configure the computer system to carry out further features of the method as set out above in relation to the first aspect.

The computer system may comprise an ultrasound imaging device. The instructions may configure the computer system to use an ultrasound transducer of the ultrasound imaging device to carry out various features of the method, e.g. to obtain the ultrasound image of the biological tissue including the object, and/or to obtain the second ultrasound image of the biological tissue including the object after the gain correction has been applied to the ultrasound scanner. Alternatively, the computer system may apply the method as set out above to a data set previously generated by an ultrasound scanner to provide an ultrasound image having reduced enhancement and/or shadowing artefact(s).

Viewed from a third aspect, the present invention provides an apparatus for reducing an artefact in an ultrasound image of biological tissue, the biological tissue comprising an object that has different attenuation than surrounding tissue, (e.g. wherein the object comprises a cyst, a ventricle, a fluid-filled cavity, or a natural or surgically-created opening), the apparatus comprising a computer system configured to carry out the method of the first aspect.

Thus, the computer system of this aspect may be configured to: obtain an ultrasound image of the biological tissue including the object that has different attenuation than the surrounding tissue; identify the object in the ultrasound image; identify a region of the ultrasound image that has an enhancement or shadowing artefact caused by the different attenuation of the object, wherein the region is identified based on one or more of: geometry of a transducer used to obtain the ultrasound image, a beam angle of transmitted ultrasound pulse(s) used to obtain the ultrasound image, and a distance of propagation of the ultrasound pulse(s) in the object; and apply a spatially varying gain correction to the identified region to compensate for the difference in attenuation of the object.

The computer system may optionally be configured to carry out further features of the method as set out above.

The apparatus may further comprise an ultrasound imaging device including an ultrasound transducer. The ultrasound imaging device may be configured to carry out further features of the method, e.g. obtaining the first and/or second ultrasound image.

Certain embodiments will now be described by way of example only and with reference to the accompanying drawings, in which.

Figure 1D:
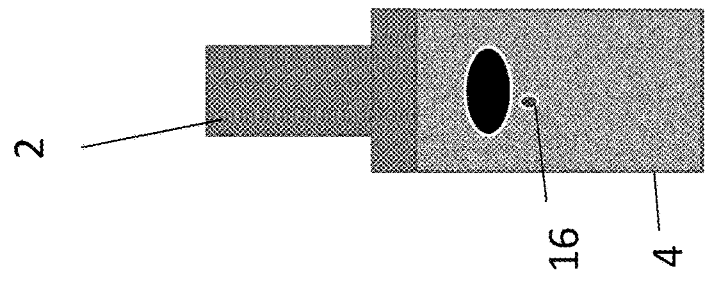
FIGS. 1A-1D show steps in a method of reducing an image artefact in an ultrasound image of a cyst.
Figure 1C:
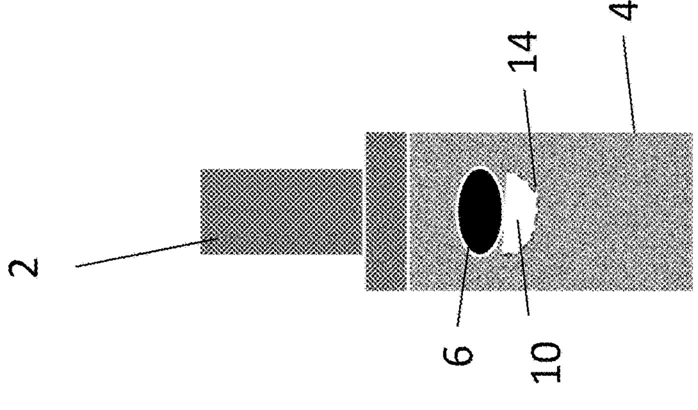
Figure 1B:
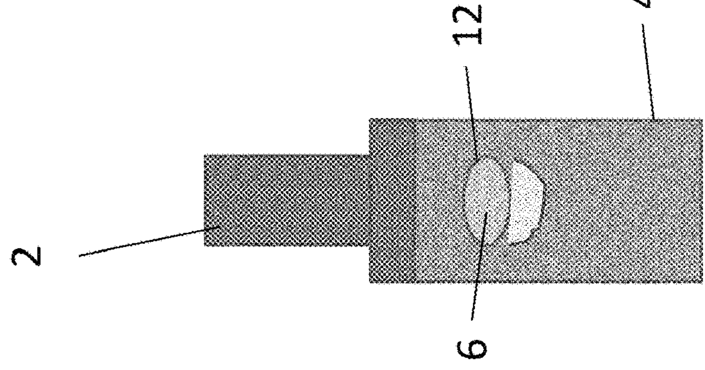
Figure 1A:
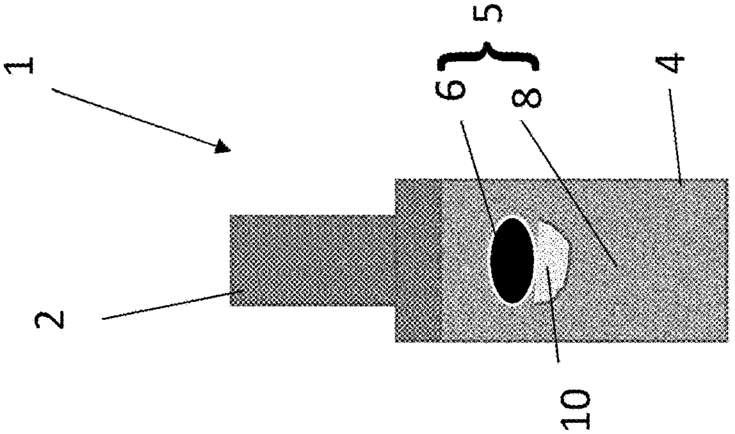

An exemplary system 1 is shown in FIG. 1A, in which a linear ultrasound transducer 2 is used to obtain an ultrasound image 4 of biological tissue 5 including a cyst 6 and surrounding tissue 8. Although the following examples are described in the context of imaging the cyst 6, the present method and system can be applied to imaging any object that has different attenuation than surrounding tissue, such as a ventricle, a fluid-filled cavity, or a natural or surgically-created opening.

An enhancement artefact 10 is visible in the ultrasound image 4 below the cyst 6 (i.e. "below" with respect to the transducer surface). The cyst 6 has lower acoustic attenuation than the surrounding tissue 8, causing the artefact 10 to form due to reduced attenuation of ultrasound pulses during propagation in the cyst 6.

The present invention provides a method of reducing the image artefact 10 by applying a gain correction to compensate for the different attenuation of the cyst 6, as shown in FIGS. 1B to 1D.

FIG. 1B shows a step of the method in which the cyst 6 is identified by detecting the boundary 12 of the cyst 6.

As shown in FIG. 1C, the method then includes identifying a region 14 of the ultrasound image 4 that includes the enhancement artefact 10 caused by the different attenuation of the cyst 6. The identified region 14 is shown by a dotted line. Exemplary ways of identifying this region 14 are described later with reference to FIGS. 2, 3 and 4.

A spatially varying gain correction is then applied to the identified region 14 to compensate for the reduced attenuation of the cyst 6. After the spatially varying gain compensation is applied, as shown in FIG. 1D, the image artefact 10 is reduced or removed. In this example, an anatomical structure 16 that was previously masked by the enhancement artefact 10 is now visible because the artefact 10 has been reduced. The corrected image 4 can now be used to make accurate medical diagnoses.

Figure 2:
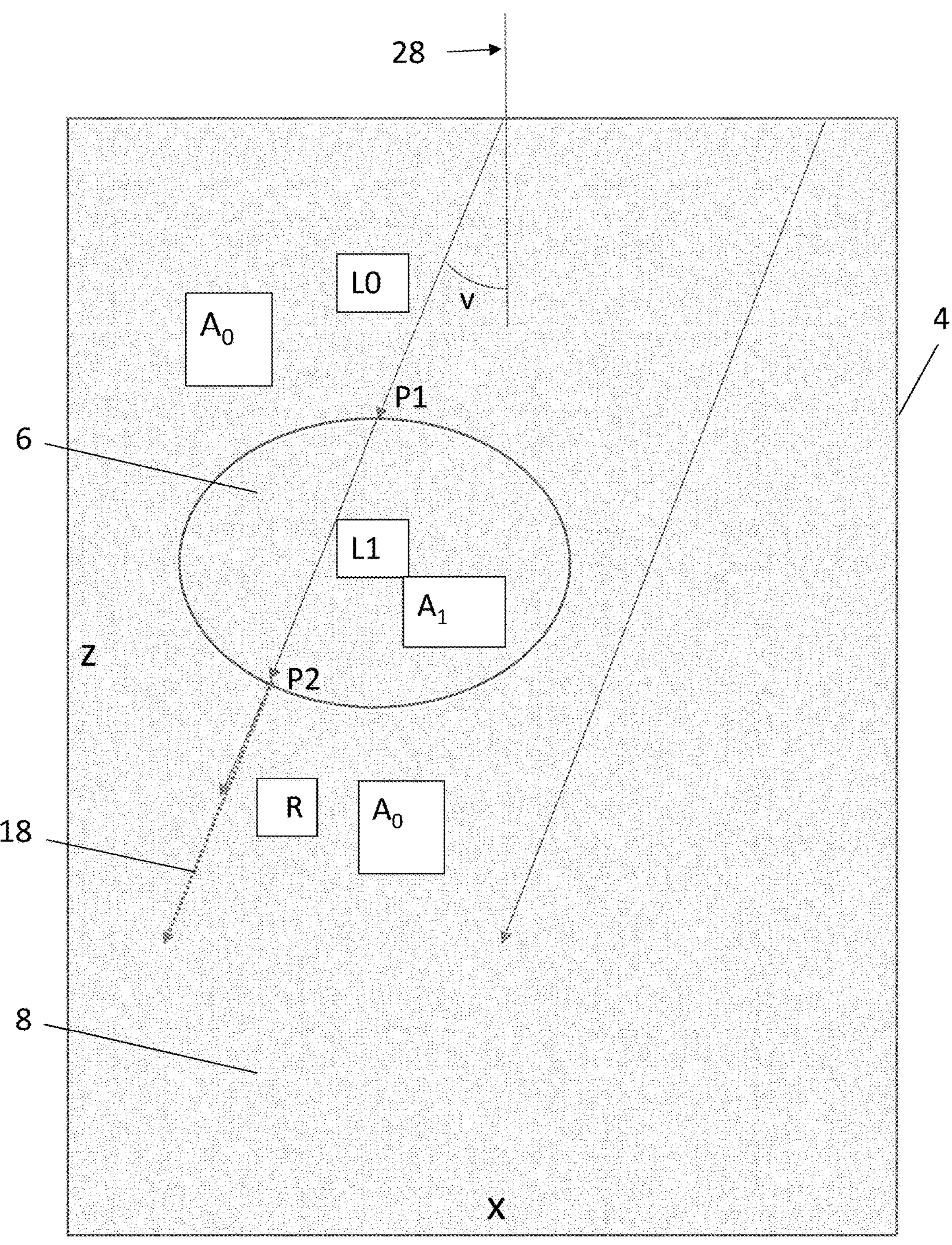
FIG. 2 shows a diagram depicting the geometry of the cyst with respect to the transducer.

The region 14 to which the gain correction is applied is identified based on one or more of: geometry of the transducer 2 used to obtain the ultrasound image 4, a beam angle of transmitted ultrasound pulse(s) used to obtain the ultrasound image 4, and a distance of propagation of the ultrasound pulse(s) in the cyst 6. The spatial relationship between the transducer and the cyst can also be used to calculate the gain correction. FIG. 2 shows how the geometry of the cyst 6 and the transducer 2 used to image the cyst 6 can be analysed to calculate the gain correction.

The cyst 6 has attenuation coefficient A1, and the surrounding tissue 8 has attenuation coefficient A0.

The gain correction factor for a pixel at depth (z) and lateral position (x) in the 2D space defined by the ultrasound image 4 can be estimated by considering the sum of attenuation experienced by the ultrasound pulses contributing to the given pixel intensity. In this example, the transducer 2 emits an ultrasound pulse having a frequency range and central frequency f0 [MHz]. The pulse propagates along a trajectory 18 in the tissue 8 with a given beam angle v with respect to the axis 20 of the transducer.

P1 is the point at which the ultrasound pulse reaches the cyst 6, and P2 is the point at which the ultrasound pulse exists the cyst 6. The pulse travels distance L0 from the transducer to P1; distance L1 from point P1 to P2; and distance R after exiting the cyst 6.

The total attenuation ATN in dB experienced by the ultrasound pulse at point P1, as compared to the intensity I at the transducer surface, can be expressed as:

$$ATN(P1) = A0 * L0 * f0 \tag{2}$$

The ultrasound pulse propagating from point P1 to P2 along distance L1 [cm] in the cyst 6 with attenuation coefficient A1 [dB/(cm MHz)] will experience an attenuation estimated as:

$$ATN(P2) = A1 * L1 * f0 \tag{3}$$

For any depths beyond P2 along the given trajectory 18 the intensities can be adjusted for the difference in attenuation coefficient A1 compared to A0 by estimating the difference in attenuation. For P2 this difference ATN_D can be expressed as:

$$\text{ATN\_D}(P2) = (A1 - A0) * L1 * f0 \tag{4}$$

For any distance R along the trajectory 18 away from the location P2, the apparent difference in attenuation for an ultrasound pulse propagating in the biological tissue 5 having areas of different attenuation (A0, A1) compared to an ultrasound pulse propagating an equivalent distance in a homogeneous medium with attenuation coefficient A0 can be expressed, using equation (1) above, as:

$$\text{ATN\_D}(R) = (A1 - A0) * (L1 - R) * f0 \tag{1}$$

The gain correction is applied to compensate for the difference in attenuation. The gain correction can be applied to all echoes received along the given beam angle v, for distances R equal or less than L1. This process is repeated for ultrasound pulses having other beam angles.

By this approach (i.e. estimating the total attenuation based on known or relative differences in attenuation coefficients A0, A1 of the media) it is possible to adjust the intensity of the pixels in the identified region 14 to compensate for the attenuation in the cyst 6. The gain correction can be defined as the inverse of the found attenuation.

Figure 3:
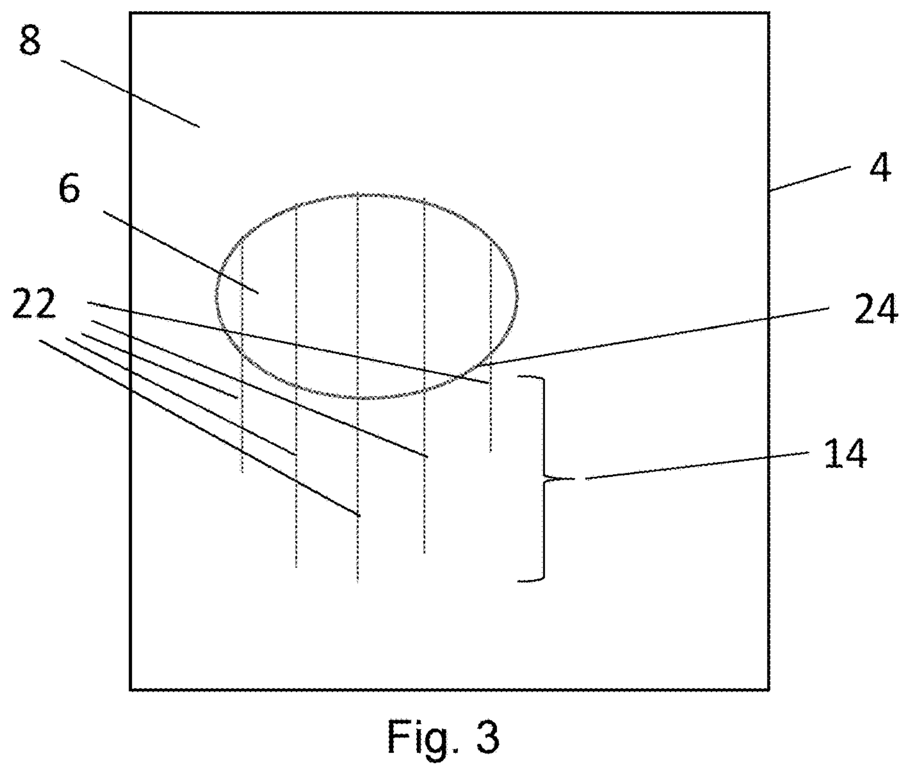
FIG. 3 shows a diagram of identifying a region of interest for a transducer having a flat linear array.
Figure 4:
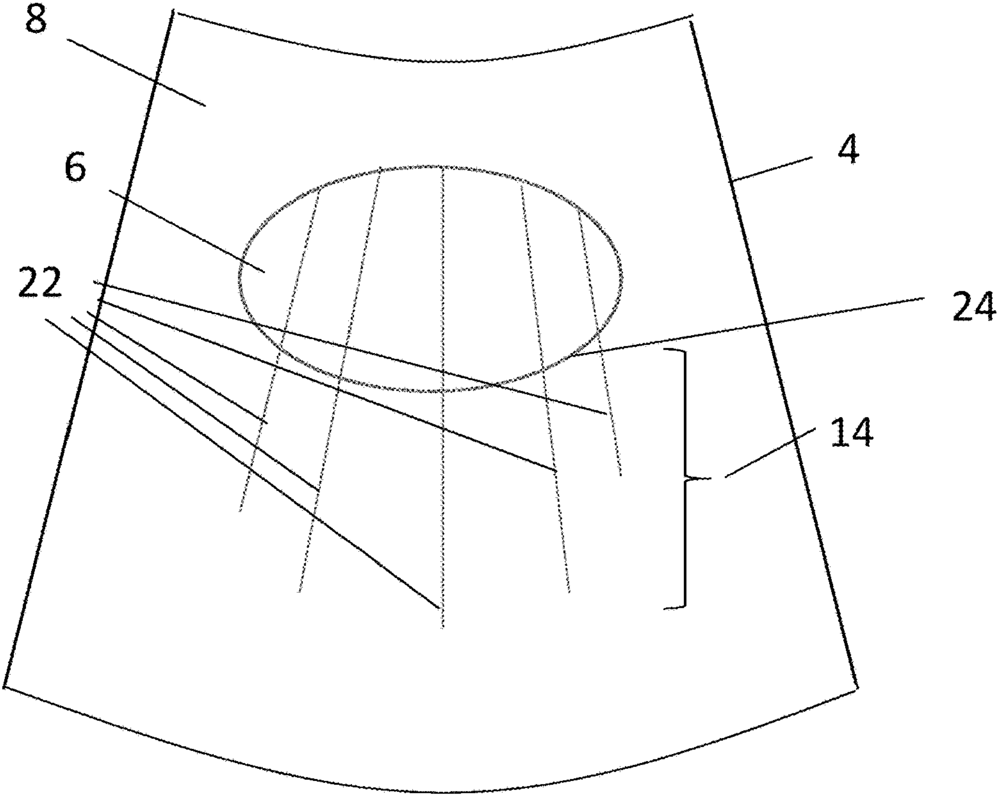
FIG. 4 shows a diagram of identifying a region of interest for a transducer having a curved linear array.

FIGS. 3 and 4 show how the region 14 to which the gain correction factor is applied can be identified based on mirroring the ultrasound pulse propagation within the cyst 6.

FIG. 3 shows the cyst 6 within surrounding tissue 8. The cyst 6 has been imaged using an ultrasound transducer (not shown). Five ultrasound pulses 22 are shown, propagating along the axial direction of the transducer. The beam angle is 0 in this case because the transducer used has a flat linear array.

To identify the region of interest 14, for each ultrasound pulse 22, the distance the pulse has travelled in the cyst 6 is determined. The path of the pulse 22 within the cyst 6 is then reflected around the lower boundary 24 of the cyst 6, to form a mirrored path of corresponding length extending from the lower boundary 24 along the same trajectory (i.e. at the same beam angle) as the pulse 22.

The gain correction is then applied to ultrasound pulses within the mirrored path region. That is, referring to FIG. 2, the gain correction is applied to echoes received along the given beam angle for distances R equal or less than L1.

FIG. 4 shows the cyst 6 within surrounding tissue 8. The cyst 6 has been imaged using a transducer (not shown) having a curved linear array. Five ultrasound pulses 22 are shown, propagating at different beam angles relative to the axis of the transducer (which in this case is the vertical direction).

To identify the region of interest 14, for each ultrasound pulse 22, the distance the pulse 22 has travelled in the cyst 6 is determined. The path of the pulse 22 within the cyst 6 is then reflected around the lower boundary 24 of the cyst 6, to form a mirrored path of corresponding length extending from the lower boundary 24 along the same trajectory (i.e. at the same beam angle) as the pulse 22.

The gain correction is then applied to ultrasound pulses within the mirrored path region. That is, referring again to FIG. 2, the gain correction is applied to echoes received along the given beam angle for distances R equal or less than L1.

Figure 5:
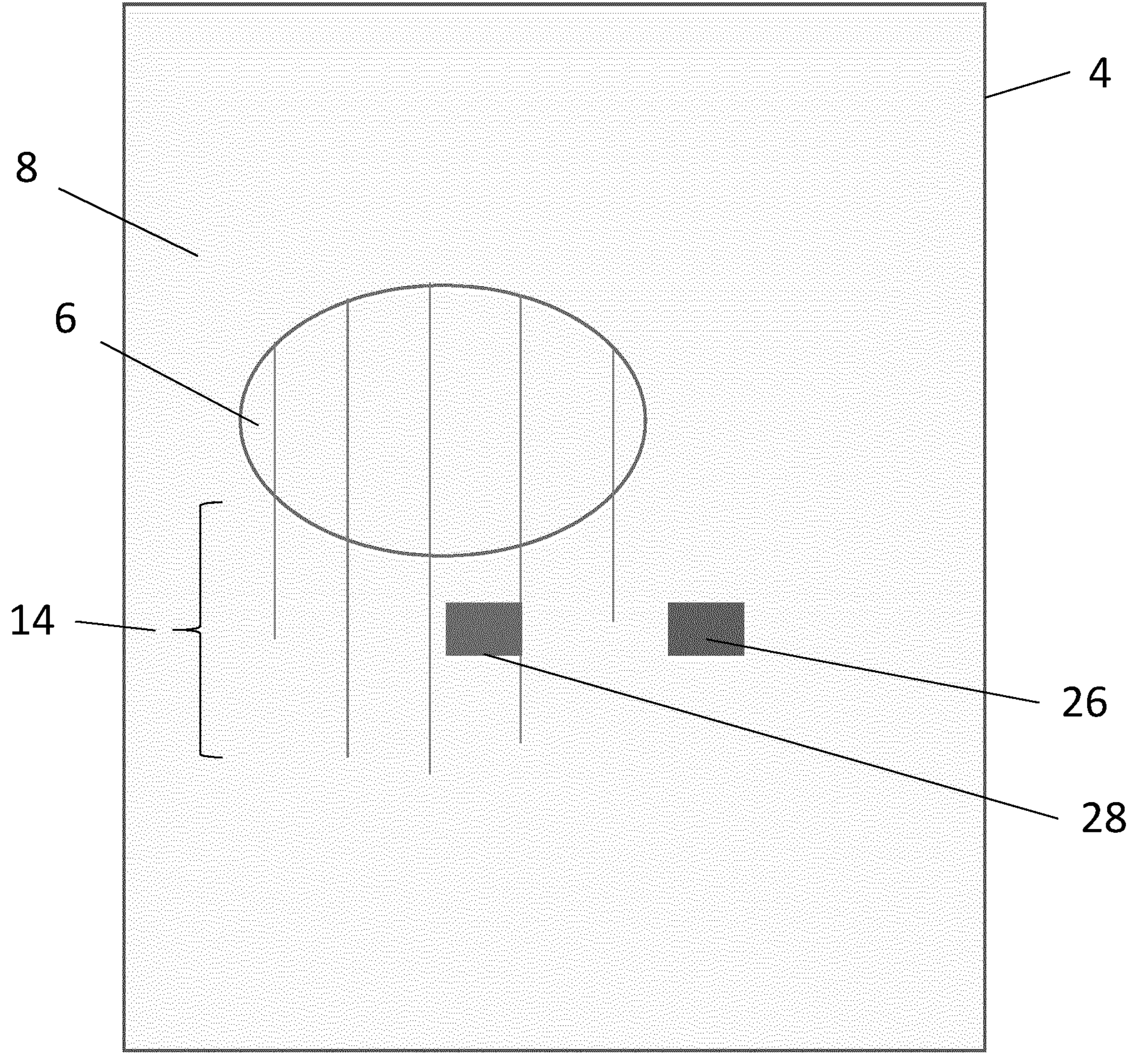
FIG. 5 shows a diagram of calculating a gain correction by comparing a first area affected by an image artefact and a second area not affected by an image artefact for a transducer having a flat linear array.

FIG. 5 shows the ultrasound image 4 of the cyst 6 imaged using a transducer (not shown) having a flat linear array. The region 14 to which the gain correction should be applied has been identified as described in FIG. 3. For simplicity, the image artefact is not shown, but it is located below the cyst 6.

The gain correction to be applied to the identified region 14 is calculated based on minimising a difference in intensity between a first area 26 of the ultrasound image 4 that is not affected by the artefact and a second area 28 of the ultrasound image 4 that is affected by the artefact. The first area 26 and second area 28 are at a similar depth in the ultrasound image 4, i.e. at a similar distance from the transducer surface.

The invention claimed is:

1. A method for reducing an artefact in an ultrasound image of biological tissue, the biological tissue comprising an object that has different attenuation than surrounding tissue, wherein the object comprises a cyst, a ventricle, a fluid-filled cavity, or a natural or surgically-created opening; the method comprising:

obtaining an ultrasound image of the biological tissue including the object that has different attenuation than the surrounding tissue;

identifying the object in the ultrasound image;

identifying a region of the ultrasound image that has an enhancement or shadowing artefact caused by the different attenuation of the object, wherein the region is identified based on one or more of: geometry of a transducer used to obtain the ultrasound image, a beam angle of transmitted ultrasound pulse(s) used to obtain the ultrasound image, and a distance of propagation of the ultrasound pulse(s) in the object; and applying a spatially varying gain correction to the identified region to compensate for the difference in attenuation of the object, wherein the gain correction is determined by:

(i) minimizing a difference in intensity between the region of the ultrasound image that has an enhancement or shadowing artefact caused by the different attenuation of the object and a region of the ultrasound image that is not affected by the artefact, wherein the region of the ultrasound image that has the enhancement or shadowing artefact and the region of the ultrasound image that is not affected by the artefact are at a similar depth; wherein the region of the ultrasound image that is not affected by the artefact comprises multiple areas positioned in a grid arrangement or one or more windows sliding over the region that has the enhancement or shadowing artefact; or (ii) based on an apparent difference in attenuation for an ultrasound pulse propagating in the biological tissue including the object and the surrounding tissue compared to an ultrasound pulse propagating an equivalent distance in a homogeneous tissue, the homogenous tissue having the same attenuation coefficient as the surrounding tissue, wherein the apparent difference in attenuation is calculated as:

$$ATN\_D(R)=(A1-A0)*(L1-R)*f0$$

wherein R is the distance along a trajectory of the ultrasound pulse away from a point at which the ultrasound pulse exits the object, A1 is the attenuation coefficient of the object, A0 is the attenuation coefficient of the surrounding tissue and the homogeneous tissue, L1 is the distance the ultrasound pulse travels in the object along the given trajectory, and f0 is a frequency of the ultrasound pulse;

wherein the gain correction is applied in real-time to an ultrasound scanner, and wherein the method comprises subsequently using the ultrasound scanner to obtain a second ultrasound image of the biological tissue including the object.

2. The method of claim 1, wherein identifying the object in the ultrasound image comprises using one or more image segmentation methods to detect a boundary of the object.

3. The method of claim 2, wherein the one or more image segmentation methods are based on at least one of machine learning, model based methods, threshold segmentation, region growing, and/or edge enhancement and edge detection methods or any combination thereof.

4. The method of claim 2, wherein identifying the region of the ultrasound image comprises mirroring the propagation of the ultrasound pulse(s) within the object with respect to the detected boundary of the object.

5. The method of claim 1, wherein the gain correction is frequency dependent.

6. The method of claim 1, comprising determining the gain correction based on a time of travel of the ultrasound pulse(s) at a given depth and a time of travel of the ultrasound pulse(s) in the object.

7. The method of claim 1, comprising determining the gain correction based on pixel intensities in one or more surrounding areas of the ultrasound image that are not affected by the enhancement or shadowing artefact.

8. The method of claim 1, comprising determining a gain correction factor for a pixel at depth (z) and lateral position (x) in the ultrasound image based on a sum of attenuation experienced by the ultrasound pulse(s) contributing to a given pixel's intensity.

9. The method of claim 8, wherein the sum of attenuation is calculated based on assumed attenuation coefficients of the biological tissue along a given path of the ultrasound pulse(s) that contribute to the given pixel intensity.

10. The method of claim 1, wherein the ultrasound image is recorded, and wherein the gain correction is applied by processing the recorded ultrasound image using computer-implemented image processing techniques.

11. A computer programme product comprising instructions that, when executed, will configure a computer system to carry out the method of claim 1.

12. The computer program product of claim 11, wherein the computer system includes an ultrasound imaging device, and wherein the instructions will configure the computer system to use a transducer of the ultrasound imaging device to obtain the ultrasound image of the biological tissue including the object.

13. An apparatus reducing an artefact in an ultrasound image of biological tissue, the biological tissue comprising an object that has different attenuation than surrounding tissue, wherein the object comprises a cyst, a ventricle, a fluid-filled cavity, or a natural or surgically-created opening, the apparatus comprising:

a computer system configured to carry out the method of claim 1.

14. The apparatus of claim 13, wherein the computer system comprises an ultrasound imaging device including a transducer configured for obtaining the ultrasound image.

* * * * *